United States Patent [19]

Hallgren

[11] 4,361,519

[45] * Nov. 30, 1982

[54] CATALYTIC ALIPHATIC CARBONATE PROCESS

[75] Inventor: John E. Hallgren, Scotia, N.Y.

[73] Assignee: General Electric Company, Schenectady, N.Y.

[*] Notice: The portion of the term of this patent subsequent to May 6, 1997, has been disclaimed.

[21] Appl. No.: 196,580

[22] Filed: Oct. 14, 1980

Related U.S. Application Data

[63] Continuation-in-part of Ser. No. 38,907, May 14, 1979, abandoned.

[51] Int. Cl.$^3$ .............................................. C07C 69/96
[52] U.S. Cl. .................................................. 260/463
[58] Field of Search ........................................ 260/463

[56] References Cited

U.S. PATENT DOCUMENTS 3,846,468  11/1974  Perrotti et al. ...................... 260/463
4,201,721  5/1980  Hallgren ............................ 260/463

*Primary Examiner*—Anton H. Sutto
*Attorney, Agent, or Firm*—James C. Davis, Jr.

[57] ABSTRACT

A catalytic aliphatic carbonate process which comprises contacting an alcohol, carbon monoxide, a Brönsted base, a Group VIIIB element selected from ruthenium, rhodium, palladium, osmium, iridium or platinum, oxygen and a redox co-catalyst. The resulting monocarbonates are useful in the preparation of polycarbonates via transesterification techniques.

9 Claims, No Drawings

CATALYTIC ALIPHATIC CARBONATE PROCESS

CROSS-REFERENCE TO RELATED APPLICATIONS

This application is a continuation-in-part of U.S. patent application Ser. No. 38,907 filed May 14, 1979, now abandoned.

BACKGROUND OF THE INVENTION

1. Field of the Invention

This invention relates to a catalytic aliphatic carbonate process which comprises contacting an alcohol, carbon monoxide, a Brönsted base, a Group VIIIB element selected from ruthenium, rhodium, palladium, osmium, iridium or platinum, oxygen and a redox cocatalyst.

2. Description of the Prior Art

Mador et al., in U.S. Pat. No. 3,114,762, issued Dec. 17, 1963, describes the preparation of aliphatic carbonates by the reaction of aliphatic alcohols with carbon monoxide carried out in the presence of a salt of palladium or platinum metal. Mador's process produces undesirable by-products including ethers and alkyl halides. Mador's patent fails to describe the use of oxygen as an essential catalyst process component in an aliphatic carbonate process in order to avoid the formation of undesirable ether and/or alkyl halide by-products.

M. Graziani et al., Journal of Organometallic Chemistry, Vol. 27 (1971), pages 275–278, describes the preparation of diethyl carbonate, ethyl chlorocarbonate, ethyl acetate and unknown reaction products—where reaction products vary in accordance with the reactants used by Graziani and the order of addition of the reactants to the reaction environment. Graziani fails to describe the use of oxygen as an essential ingredient in a reaction route leading to the formation of ethyl carbonate in order to avoid the formation of undesirable ethyl chlorocarbonate, ethyl acetate, and an unidentified reaction product.

Perrotti et al. in U.S. Pat. No. 3,846,468, issued Nov. 5, 1974, later reissued as U.S. Pat. No. Re. 29,338 on Aug. 2, 1977 describes the preparation of carbonic acid esters by the stoichiometric reaction of an aliphatic alcohol with carbon monoxide and oxygen carried out in the presence of copper complexed with a Lewis base, i.e. an electron donor species, e.g. pyridyl, dipyridyl, imidazole, phenanthroline, alkyl or aryl phosphines, dimethylsulfoxide, dimethylformamide, quinuclidine, $CH_3CN$, $C_6H_5CN$, malonitrile, succinodinitrile, adiponitrile, etc. Perrotti's Lewis bases function as electron donor species which basic species form complexes with the metals (M) of the IB, IIB, and VIII of the periodic system. When Perrotti's Lewis base species are substituted for the Brönsted bases in my process Perrotti's Lewis bases—as suggested by Perrotti—coordinate with my Group VIIIB elements with the result that no aliphatic carbonate is formed. Wherein Brönsted bases are defined herein and in the appended claims the use of the term "Brönsted base" is intended to expressly exclude the use of Perrotti's Lewis bases within the scope of my process. Carbon monoxide—not functional as a Lewis base in my process—is of course included as a reactant in my process. Perrotti's process requires the sequential addition of oxygen followed by carbon monoxide.

Unexpectedly, I have found that aliphatic carbonates can be formed in a catalytic process when alcohols are carbonylated in the presence of oxygen and a Brönsted base, i.e. a proton acceptor species, e.g. sodium hydroxide, sodium methoxide, triethylamine, dioctylbenzylamine, 1,2,2,6,6-pentamethylpiperadine, etc. My Brönsted bases function as a proton acceptor species, i.e. basic species which do not form complexes with the VIIIB elements employed in my process. Accordingly, wherein Brönsted bases as defined herein are used in my process it is to be understood that my Brönsted bases do not form legand complexes with my VIIIB elements and—in contradistinction to Perotti—function as proton acceptors of hydrogen derived from the alcohol reactant. My catalytic process provides aliphatic carbonates while avoiding the formation of undesirable by-products, e.g. alkyl halides, ethers, esters, etc., without requiring the sequential addition of reactants, e.g. oxygen and carbon monoxide, as described by Perrotti.

DESCRIPTION OF THE INVENTION

This invention embodies a catalytic aliphatic carbonate process which comprises contacting an alcohol, carbon monoxide, a Brönsted base, a Group VIIIB element selected from ruthenium, rhodium, palladium, osmium, iridium or platinum, oxygen and a redox cocatalyst.

An alcohol is defined herein and in the appended claims as any hydroxy-substituted aliphatic including cycloaliphatic compound. Illustratively, an alcohol or alcoholic reactant can be described by the formula $$R_b\text{--}(OH)_x, \qquad (I)$$

wherein $R_b$ represents an aliphatic radical wherein an —OH radical (also referred to herein as a group) is attached directly to an aliphatic carbon atom and x is a whole number equal to at least 1, preferably from 1–3. The alcohol defined by Formula (I) above includes primary, secondary, or tertiary alkanols,—as well as, but not limited to—carbo-monocyclic, carbo-polycyclic or fused carbo-polycyclic alcohol systems which may be connected to each other by single or double valence bonds or bi- or multivalent radicals. Included within the expression "alcohol" are organic compounds containing—both aliphatic and aromatic carbon atoms—where at least one hydroxy substituent is attached to a carbon atom whose chemical properties are aliphatic as opposed to aromatic, e.g. benzyl alcohol.

Preferred aliphatic alcoholic reactants are often alcohols of the general formula:

$$C_nH_{2n+2-z}(OH)_z, \qquad (II)$$

wherein n is a whole number of from 1–30, preferably 1–20, and still more preferably 1–10, and wherein z is a whole number of from 1–3, preferably from 1–2, and more preferably 1. Illustrative of commercially important alcoholic reactants included within the above description are the following: methanol; ethanol; 1-propanol; 2-propanol; 1-butanol; 2-methyl-1-propanol (isobutyl alcohol); 1-hexanol; 1-octanol; 2-ethyl-1-hexanol; isooctyl alcohol; 1-decanol; isotridecyl alcohol; 1-octoadecanol (stearyl alcohol); 1,2-ethanediol (ethylene glycol); 2,2-oxydiethanol (diethylene glycol); triethylene glycol; tetraethylene glycol; 1,2-propanediol (propylene glycol); dipropylene glycol; 1,3-propanediol; 1,4-butanediol; 1,5-pentanediol; glycerol (1,2,3-propanetriol); 1,1,1-trimethylolethane (2-hydroxymethyl-2-methyl-1-1,3-propanediol); 1,1,1-trimethylolpropane (2-ethyl-2-hydroxymethyl-1,3-propanediol); pentaerythritol (2,2-bis(hydroxymethyl)-1,3-propanediol); sorbitol (D-glucitol); 1,2,6-hexanetriol; and methyl glucoside. Especially presently preferred are $C_{1-4}$ aliphatic alcohols, i.e. methanol, ethanol, propanol and butanol.

Any Group VIIIB element, defined herein and in the appended claims as "the Group VIIIB element" can be emplyed subject to the proviso that the element be selected from ruthenium, rhodium, palladium, osmium, iridium, or platinum. The Group VIIIB element can be employed in any oxidation state including oxidation states of zero, plus one, plus two, etc.

The Group VIIIB elements can be present in ionic, inorganic or organic compound or complex, etc., forms. The Group VIIIB elements can be employed in oxide, halide, nitrate, sulfate, oxalate, acetate, carbonate, propionate, hydroxide, tartrate, etc., forms.

Group VIIIB elements in complex form, e.g., with ligands, such as carbon monoxide, nitriles, tertiary amines, phosphines, arsines, or stibines, etc., can be employed and illustratively are often represented by those skilled in the art as mono-, di-, or polynuclear Group VIIIB element forms. Generally, the dimeric or polymeric forms are considered to contain Group VIIIB atoms bridged by ligands, halogens, etc. Preferred Group VIIIB elements form homogeneous mixtures when combined with the reactants, especially when the process is carried out under liquid phase reaction conditions.

The Group VIIIB elements, compounds and/or complexes can be prepared by any method well-known to those skilled in the art including the methods referenced in the following publication:

*Reactions of Transition-Metal Complexes,* J. P. Candlin, K. A. Taylor and D. T. Thompson, Elseivier Publishing Co. (1968) Library of Congress Catalog Card No. 67-19855 as well as those described in various U.S. and foreign technical journals and patents.

Illustrative of generally presently preferred Group VIIIB elements, compounds or complexes that can be used in my process follow: Ru, $RuCl_2$, $RuBr_2$, $RuI_2$, $Ru(CO)_2Cl_2$, $Ru(CO)_2I_2$, $Ru(CO)_4Cl_2$, $Ru(CO)_4Br_2$, $Ru(CO)_4I_2$, $RuCl_3$, $RuBr_3$, $RuI_3$, etc., Pd, $PdCl_2$, $PdBr_2$, $PdI_2$, $[Pd(CO)Cl_2]_2$, $[Pd(CO)Br_2]_2$, $[Pd(CO)I_2]_2$, $(C_6H_5CN)_2PdCl_2$, $PdCl_4$, $Pd(OH)_2(CNC_4H_9)_2$, $PdI_2(CNC_6H_5)_2$, $Pd(OH)_2(CNCH_3OC_6H_5)_2$, $Pd(CNC_4H_9)_4$, etc., Rh, $Rh(CO)Cl_2$, $Rh(CO)Br_2$, $Rh(CO)I_2$, $Rh_2Cl_2(CO)_2$, $Rh_2(CO)_4Cl_2$, $Rh_2(CO)_4Br_2$, $Rh_2(CO)_4I_2$, $[Rh(CO)_2Cl]_2$, $RhCl_3$, $RhBr_3$, $RhI_3$, etc., Os, $Os(CO)_3Cl_2$, $Os(CO)_3Br_2$, $Os(CO)_3I_2$, $Os(CO)_4Cl_2$, $Os(CO)_4Br_2$, $Os(CO)_4I_2$, $Os(CO)_8Cl_2$, $Os(CO)_8Br_2$, $Os(CO)_8I_2$, $OsCl_2$, $OsCl_3$, $OsI_2$, $OsI_3$, $OsBr_3$, $OsBr_4$ and $OsCl_4$, etc., Ir, $IrCl_3$, $IrCl_3(CO)$, $Ir_2(CO_8)$, $IrCl_3$, $IrBr_3$, $IrBr_4$, $IrI_4$, etc., $PtCl_2$, $PtBr_2$, $PtI_2$, $Pt(CO)_2Cl_2$, $Pt(CO)_2Br_2$, $Pt(CO)_2I_2$, $Pt(CO)Cl_4$, $Pt(CO)_2Br_4$, $Pt(CO)_2I_4$, $Pt(CO)_3Cl_4$, $Pt(CO)_3Br_4$, $Pt(CO)_3I_4$, $PtCl_2(CNC_6H_5)_2$, etc.

This process is carried out in a Brönsted basic reaction medium, i.e. a reaction environment which employs any inorganic or organic base including mixtures thereof which do not form ligand complexes with the VIIIB elements employed in this process. Representative of basic species—classified herein and in the appended claims as Brönsted bases, i.e. proton acceptors—which can be employed are the following: elemental alkali and alkaline earth metals; basic quaternary ammonium, quaternary phosphonium or tertiary sulfonium compounds; alkali or alkaline earth metal hydroxides or alkoxide; salts of strong bases and weak acids; primary, secondary, tertiary amines; as well as sterically hindered amines, etc. Specific examples of the aforementioned are sodium, potassium, magnesium metals, etc.; quaternary ammonium hydroxide, tetraethyl phosphonium hydroxide, etc.; sodium, potassium, lithium, and calcium hydroxide; quaternary phosphonium, tertiary sulfonium, sodium, lithium, and barium carbonate; sodium acetate; sodium benzoate; sodium methylate; sodium thiosulfate; sodium sulfide; sodium tetrasulfide; sodium cyanide; sodium hydride; sodium borohydride; potassium fluoride; trimethylamine, triethylamine; allyldiethylamine; benzyldimethylamine; dioctylbenzylamine; 1-dimethylamino-2-phenylpropane; N, N, N', N'-tetramethylenediamine; 2,2,6,6-tetramethylpiperidine, N-methyl-piperidine; 1,2,2,6,6-pentamethylpiperidine; etc. Generally preferred are alkali or alkali earth metal bases, especially alkali or alkaline earth metal hydroxides or alkoxides.

In this process oxygen is employed as the sole oxidant in combination with a redox co-catalyst selected from a periodic Group element, compound or complex. Any source of oxygen can be employed, i.e., air, gaseous oxygen, liquid oxygen, ozone etc. Preferably either air or gaseous oxygen is employed.

The redox co-catalysts as a class comprise any element, compound or complex which catalyze the oxidation of "the Group VIIIB element," i.e., ruthenium, rhodium, palladium, osmium, iridium or platinum, in the presence of oxygen from a lower oxidation state to a higher oxidation state. Preferred redox co-catalysts comprise elements, compounds or complexes of a periodic Group IIIA, IVA, VA, VIA, VIIA, IB, IIB, VB, VIB, VIIB, VIIIB, lanthanide or actinide.

As used herein and in the appended claims, the expression "complexes" includes coordination or complex compounds well-known to those skilled in the art such as those described in *Mechanisms of Inorganic Reactions,* Fred Basolo and Ralph G. Pearson, 2nd Edition, John Wiley and Sons, Inc. (1969). These compounds are generally defined herein as containing a central ion or atom, i.e., a periodic Group IIIA, IVA, VA, VIA, VIIA, IB, IIB, IVB, VB, VIB, VIIB, VIIIB, lanthanide or actinide element and a cluster of atoms or molecules surrounding a periodic group element. The complexes may be nonionic, or a cation or anion, depending on the charges carried by the central atom and the coordinated groups. The coordinated groups are defined herein as ligands, and the total number of attachments to the central atom is defined herein as the coordination number. Other common names for these complexes include complex ions (if electrically charged), Werner complexes, coordination complexes or, simply, complexes.

This process is carried out under positive oxygen pressure, i.e., where oxygen is present in stoichiometric amounts sufficient to form the desired aliphatic carbonate. In general, oxygen pressures within the range of from about 0.1 or lower, to 500 atmospheres, or even higher, can be employed with good results. Presently preferred are oxygen pressures within the range of from about ½ to 200 atmospheres.

Any amount of oxygen can be employed. For example, oxygen to alcohol mole proportions within the range of from about 0.001:1 or lower to about 1000:1 or higher are effective, however, preferably ratios from 0.1:1 to 10:1 are employed to insure an optimum conversion of alcohol to aliphatic carbonate.

Any amount of redox co-catalyst component can be employed. For example, redox co-catalyst to alcohol mole proportions within the range of from about 0.0001:1 or lower to about 1000:1 or higher are effective; however, preferably ratios of from 0.0001:1 to 1:1, and more preferably 0.001:1 to 0.01:1 are employed.

Any amount of base can be employed. In general, effective mole ratios of base to "the Group VIIIB element" are within the range of from about 0.00001:1 to about 100:1 or higher, preferably from 0.5:1 to about 10:1, and more preferably from 1:1 to 2:1. Generally, mole ratios of at least 1:1 enhance both the reaction rate and the yield of aliphatic carbonate.

Any amount of "The Group VIIIB element" can be employed. For example, "the Group VIIIB element" to alcohol mole proportions within the range of from about 0.0001:1 or lower to about 1000:1 or higher are effective; however, preferably ratios of from 0.001 to 0.01 are employed.

Any amount of carbon monoxide can be employed. Preferably the process is carried out under positive carbon monoxide pressure; i.e., where carbon monoxide is present in stoichiometric amounts sufficient to form the desired aliphatic carbonate. In general, carbon monoxide pressures within the range of from about $\frac{1}{2}$ to 500 atmospheres, or even higher, can be employed with good results. Presently preferred are CO pressures within the range of from 1 to 200 atmospheres.

This process can be carried out in the absence of any solvent, e.g. where the alcohol acts as both a reactant and a solvent, however, optionally can be carried out in the presence of a solvent, preferably a solvent of the general class: methylene chloride, ethylene dichloride, chloroform, carbon tetrachloride, tetrachloroethylene, nitromethane, hexane, 3-methylpentane, heptane, cyclohexane, methylcyclohexane, cyclohexane, isooctane, p-cumene, cumene, decalin, toluene, benzene, diphenylether, dioxane, thiophene, dimethyl sulfide, ethyl acetate, tetrahydrofuran, chlorobenzene, anisol, bromobenzene, o-dichlorobenzene, methyl formate, isodobenzene, acetone, acetophenone, etc., and mixtures thereof.

Any amount of solvent, preferably inert, can be employed. In general, optimum solvent to alcohol mole proportions are from 0.5:99.5 to 99.5:0.5, preferably from 50:50 to 99:1.

Any reaction temperature can be employed. In general, optimum reaction temperatures are 0° C., or even lower, to 200° C., or even higher and more often 0° C. to 50° C.

Any reaction time period can be employed. Generally optimum reaction time periods are about 0.1 hour or even less to about 10 hours or even more.

An optional reaction parameter in the practice of this process includes substantially anhydrous reaction conditions, e.g. where any water formed during the course of the reactions involved is removed from the reaction environment by any means, such as the use of azeotropic distillation techniques, a drying agent, etc. including molecular sieves manufactured by the Linde Division of the Union Carbide Corporate generally known as zeolite types A, X and Y, described in U.S. Pat. Nos. 2,882,243, 3,130,007 and 3,529,033, which descriptions are incorporated herein in their entirety by reference. Other zeolites, of course, are included within the scope of this invention.

Any amount of drying agent can be employed and such amounts can be determined by means of routine experimentation. For example, the optimum amounts of molecular sieve required for selective absorption of water formed during the course of the process can be estimated by routine reference to Linde (R) Company, molecular Types 3A and 4A "Water Data Sheets" published and distributed by Union Carbide Corporation.

In a preferred embodiment, a manganese or cobalt redox co-catalyst is employed. Illustrative descriptions of the manganese or cobalt redox co-catalysts are found in my U.S. Pat. No. 4,201,721. For brevity their descriptions are incorporated herein in their entirety by reference.

In a still more preferred embodiment this process is carried out in a reaction environment which contains a manganese redox co-catalyst of any alpha-diketone or beta-diketone, or mixtures thereof—preferably because of their efficacy—manganese complexes associated with acetylacetone, e.g. manganese(II)-bis(acetoacetonate).

In another optional reaction parameter, this process is carried out in the presence of an organic phase transfer agent (PTA). Generally effective phase transfer agents include quaternary ammonium compounds, quaternary phosphonium compounds, tertiary sulfonium compounds, crown ether compounds, chelated cationic salts, cryptates, i.e. any agent which is soluble in the organic phase and which enhances the transfer, maintenance or retention of a halide, and in a preferred embodiment a bromide, in the organic phase in the reaction environment. Illustrative descriptions of PTA's are found in my U.S. Pat. No. 4,201,721. For brevity these descriptions are incorporated herein in their entirety by reference.

Any amount of phase transfer agent can be employed. Effective mole ratios of phase transfer agents to "the Group VIIIB element" are within the range of from about 0.00001:1 to about 1000:1 or higher, preferably from about 0.05:1 to about 100:1 and more preferably from about 10:1 to 20:1.

The following examples are illustrative of the best mode of this invention. In the examples, unless otherwise specified, all parts are by weight and the reaction products were verified by infrared spectrum, C-13 nuclear magnetic resonance and mass spectrometry.

EXAMPLE I

A 50 mol. round bottom flask—equipped with carbon monoxide and air inlets and a gas exit—was charged with a spin bar, 1.0 g. (30 mmol) of methanol, 2.0 g. of Linde 3A molecular sieves which had been activated by heating to 200° C. in a stream of dry nitrogen for 24 hours, 0.23 g. (1.5 mmol.) of 1,2,2,6,6-pentamethylpiperidine, 0.027 G. (0.1 mmol.) of palladium(II) dibromide, and 0.131 g. (0.3 mmol.) of the pyridine adduct of salicylaldehyde-ethylene diamine cobalt(II) complex. Carbon monoxide and air were bubbled through the stirred solution at room temperature for 20 hours. The reaction product—analyzed by GPC, ir and gc-ms—contained 0.032 g. (0.36 mmol.) of dimethyl carbonate.

EXAMPLES II-VI

A series of aliphatic carbonates were prepared as described in Example I except for variation of either or both the redox co-catalyst or solvent. Set out in Table I hereafter is a resume of the reaction parameters, variations from Example I, and the associated results:

TABLE I

| Example No. | Solvent | Redox Co—Catalyst Component | Percent (%) Conversion | Reaction Time (hr) | Turn[1] Over Value |
|---|---|---|---|---|---|
| II | $CH_3OH$ | Co(II) complex* | — | 20 | 3.6 |
| III | $CH_2Cl_2$ | Co(II) complex* | — | 20 | 9.3 |
| IV | $CH_2Cl_2$ | $CuCl_2$ | — | 20 | 1.0 |
| V | $CH_2Cl_2$ | Mn(II) (benzoin oxime)$_2$ | — | 18 | 0.4 |
| VI | $CH_2Cl_2$ | Mn(II) (acetylacetonate)$_3$ | — | 72 | 2.5 |

*same as Example I, i.e., the pyridine adduct of a salicylaldehyde-ethylene diamine cobalt(II) complex
[1]Turn over value = the number of carbonate moieties, i.e.

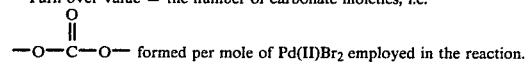 formed per mole of Pd(II)Br$_2$ employed in the reaction.

EXAMPLE VII

A 50 ml. flask equipped as in Example I, was charged with 0.46 g. (10 mmol.) of ethanol. 4.0 g. of a Linde 3A molecular sieve activated as in Example I, 0.11 g. (1.3 mmol.) of a 50% aqueous solution of sodium hydroxide, 0.027 g. (0.1 mmol) of palladium(II) dibromide, 0.11 g. (0.3 mmol.) of Mn(II) (acetylacetonate)$_3$, 0.51 g. (1.6 mmol.) of tetrabutylammonium bromide, and 25 ml. of methylene chloride. Carbon monoxide and air were bubbled through the stirred solution at room temperature for 16 hours. The reaction product—analyzed by GPC, ir and gc-ms—contained 0.33 g. (2.8 mmol.) of diethyl carbonate.

EXAMPLE VIII

A 100 ml. flask equipped as in Example I was charged with 4.6 g. (100 mmol. of ethanol, 4.0 g. of a Linde 3A molecular sieve activated as in Example I, 0.21 g. (1.3 mmol.) of a 25% aqueous solution of sodium hydroxide. The resulting solution was stirred at room temperature for one hour. Then 0.027 g. (0.1 mmol.) of palladium(II) dibromide, and 0.076 g. (0.3 mmol.) of Mn(II) (acetylacetonate)$_2$, 0.52 g. (1.6 mmol.) of tetrabutylammonium bromide, and 50 ml. of methylene chloride were added. Carbon monoxide and air were bubbled through the stirred solution at room temperature overnight. The reaction product—analyzed by GPC, in and gc-ms—contained 0.052 g. (0.44 mmol.) of diethyl carbonate.

EXAMPLE IX

A 100 ml. flask equipped as in Example I was charged with 50 ml. of absolute ethanol. 4.0 g. of a Linde 3A molecular sieve activated as in Example I and 0.24 g. (3.0 mmol.) of a 50% aqueous solution of sodium hydroxide. The resulting solution was stirred at room temperature for one hour. Then 0.027 g. (0.1 mmol.) of palladium(II) dibromide, 0.076 g. (0.3 mmol.) of Mn(II) (acetylacetonate)$_2$ and 100 ml. of benzene were added. Carbon monoxide and air were bubbled through the stirred solution at room temperature overnight. The reaction product—analyzed by GPC, ir and gc-ms—contained 0.18 g. (2.09 mmol.) of diethyl carbonate.

EXAMPLE X

A 100 ml. flask equipped as in Example I was charged with 50 ml. of absolute ethanol, 4.0 g. of a Linde 3A molecular sieve activated as in Example I, 0.24 g. (3.0 mmol.) of a 50% aqueous solution of sodium hydroxide, and 1.13 g. (3.0 mmol.) of tetrabutylammonium bromide. The resulting solution was stirred at room temperature for one hour then 0.027 g. (0.1 mmol.) of palladium(II) dibromide, 0.076 g. (0.3 mmol.) of Mn(II) (acetylacetonate)$_2$, and 100 ml. of benzene were added. Carbon monoxide and air were bubbled through the stirred solution at room temperature overnight. The reaction product—analyzed by GPC, ir and gc-ms—contained 0.122 g. (1.41 mmol.) of diethyl carbonate.

Although the above examples have illustrated various modifications and changes that can be made in carrying out my process, it will be apparent to those skilled in the art that this process includes a catalytic aliphatic carbonate process for the preparation of carbonates having the general formula:

wherein R is hydrocarbon radical selected from the class consisting alkyl or cycloalkyl radicals which comprises contacting an alcohol of the formula ROH in which R is as defined hereinbefore, carbon monoxide, a Brönsted base, a Group VIIIB element selected from ruthenium, rhodium, palladium osmium, iridium or platinum, oxygen and a redox co-catalyst.

I claim:

1. A catalytic aliphatic carbonate process for the preparation of carbonates having the general formula:

wherein R is a hydrocarbon radical selected from the class consisting of alkyl or cycloalkyl radicals, which comprises reacting under substantially anhydrous reaction conditions, an alcohol of the formula ROH in which R is as defined hereinbefore, carbon monoxide, a Bronsted base, Group VIIIB catalyst selected from ruthenium, rhodium, palladium, osmium, iridium or platinum, oxygen and a redox co-catalyst which catalyses the oxidation of the Group VIIIB catalyst in the presence of oxygen subject to the proviso that the process is carried out while introducing concurrently both carbon monoxide and oxygen to the alcohol, Bronsted base, Group VIIIB catalyst and redox co-reactants.

2. The claim 1 process wherein the alcohol is ethanol, the base is sodium hydroxide, the Group VIIIB catalyst is in the form of palladium (II) dibromide and the redox co-catalyst is manganese(II) (acetylcetonate)$_2$.

3. A catalytic aliphatic carbonate process carried out under substantially anhydrous reaction conditions and in the substantial absence of undesirable byproducts consisting essentially of reacting an alcohol, carbon monoxide, a Bronsted base, a Group VIIIB catalyst selected from ruthenium, rhodium, palladium, osmium, iridium or platinum, oxygen and a redox co-catalyst which catalyses the oxidation of the Group VIIIB catalyst in the presence of oxygen, subject to the proviso that the process is carried out while introducing concurrently both carbon monoxide and oxygen to the alcohol, Bronsted base, Group VIIIB catalyst and redox co-reactants.

4. The claim 3 process further comprising a solvent.

5. The claim 3 process wherein said catalyst oxidation state is at least +2.

6. The claim 3 process wherein said catalyst is associated with a halide.

7. The claim 3 process further comprising a molecular sieve.

8. The claim 3 process wherein said redox co-catalyst is selected from a manganese redox co-catalyst of an alpha- or a beta-diketone.

9. The claim 3 process wherein the base is selected from alkali or alkaline earth metal bases.

* * * * *